United States Patent [19]

Cerceo et al.

[11] 4,450,849

[45] May 29, 1984

[54] DENTAL PHYSIO-TAPE

[76] Inventors: Chris A. Cerceo; Jeanie F. Kaufman, both of Box AP, 3443 Lake Tahoe Blvd., Suite F, South Lake Tahoe, Calif. 95705; Martin H. Kaufman, Box 243, Ridgecrest, Calif. 93555

[21] Appl. No.: 423,860

[22] Filed: Sep. 27, 1982

[51] Int. Cl.$^3$ ............................................. A61C 15/00
[52] U.S. Cl. ..................................................... 132/89
[58] Field of Search .............................. 132/89, 93, 91

[56] References Cited

U.S. PATENT DOCUMENTS

| | | | |
|---|---|---|---|
| 174,619 | 3/1876 | Clark, Jr. ............................... | 132/89 |
| 1,637,153 | 7/1927 | Lawton ............................... | 132/93 X |
| 2,700,636 | 1/1955 | Ashton ............................... | 132/89 X |
| 3,511,249 | 5/1970 | Baitz ..................................... | 132/89 |
| 3,699,979 | 10/1972 | Muhler .................................. | 132/89 |
| 4,034,770 | 7/1977 | Trecker ................................. | 132/90 |
| 4,142,538 | 3/1979 | Thornton .............................. | 132/89 |

Primary Examiner—Gregory E. McNeill

[57] ABSTRACT

A novel dental tape for cleaning between the teeth is described. The tape is made of strong, flexible, non-tacky, non-toxic polymer which has rows of protuberances on which foreign particles between the teeth get caught and are removed as the tape is moved between the teeth.

19 Claims, 4 Drawing Figures

DENTAL PHYSIO-TAPE

FIELD OF INVENTION

This invention relates to improved dental tape which is easy to use and has excellent plaque removing capability.

BACKGROUND OF THE INVENTION

To this date, dental floss and ribbon have been used for the removal of food debris, materia alba, and bacterial plaque from the interproximal surfaces of the human dentition. The intended motion of said floss is in an occluso-gingival direction. Many adults and children find that this requires a great deal of dexterity, and thus do not effectively accomplish the intended task. There appears to be a tendency for many to "saw" the floss through the contact areas in a bucco-lingual direction. With traditional thread floss this can be damaging to the tooth at the cementoenamel junction interproximally, as the force applied is proportional to a decreased diameter of the threaded floss. This is less true of the ribbon floss. Both the threaded floss and ribbon floss plaque-removing capability is resultant to the action of the mechanical action at the free edges - occlusally and gingivally (when motion is occlusogingivally). A bucco-lingual motion of traditional floss can also damage the interdental papillary tissue filling the gingival embrasures, and if used improperly, damage can be done regardless of the motion used.

The area of the mouth of concern is the gingival embrasure. It is this area where chronic gingivitis proceeds to infiltrate the remaining periodontium to yield a resultant periodontitis.

One object of the present invention is to provide a dental tape which removes plaque with greater efficiency than traditional floss. Another object is to provide a dental tape which requires little dexterity in removing plaque by motions in occlusal, buccal, and lingual directions. Still another object is to provide a tape which has a minimum proclivity to damage the interdental papilla and attachment while permitting tape movement over a broad spectrum of gingival embrasure height. Still another object is to provide a tape having flavoring and antiseptic properties.

SUMMARY OF THE INVENTION

We have invented a unique, economical, and easily manufacturable dental tape which removes plaque from the teeth and the teeth area as the tape is pulled between the teeth. The strong, flexible, non-tacky, tear-resistant tape has a plurality, i.e. a large number or multitude of rows of solid or hollow protuberances which are aligned obliquely to the parallel edges of the tape. Hollow protuberance means an enclosed hollow within the protuberance. As the tape is drawn between the teeth, debris is caught by the protuberances and made to rise up, i.e., from the base of the teeth to the ends of the teeth, and away from the teeth by the oblique alignment of the protuberances, the lowest protuberance of a row rubs at the base of a tooth and subsequent protuberances of the row rub the tooth at greater and greater distances from the base, and foreign matter such as materia alba and bacterial plaque is dislodged by rubbing, and rides along the oblique row, being lifted and carried away from the teeth. The hollow protuberances have give, i.e., they yield under force or pressure, and can be used by people who have very sensitive gums. The tape can be made of polymeric film containing fiber reinforcement, and alternatively, can be woven from natural and synthetic thread with the protuberances provided by molding or pressing in place or sewn in place knots of thread. Tasteful, nice smelling, and antiseptic additives can be incorporated within the tape.

The present invention, further objects and advantages thereof, may best be understood by reference to the following drawings in which:

FIG. 1 shows the tape 4 having a parted perforation row 3 and unparted perforation row 3' which permits user to remove a strip of tape from a roll. The distance $d_1$ between protuberances 1 is variable as is the distance $d_2$ between rows of protuberances, and as is the angle a the rows of protuberances make with the tape's long axis. By variable is meant that the distances and angle can each assume preselected values, the variable having characteristics of a mathematical variable. One section of the tape can contain a multitude of rows of protuberances each making different angles a. While pulling the tape between the teeth, gripping the knurled sections 5 prevents slippage.

FIG. 2 illustrates a sectional cut through a typical row of protuberances as shown in FIG. 1 illustrating that the protuberances of a row begin at one edge, angularly proceed across the tape width and end at the other edge of the tape and can be on both sides of the tape, if desired. The alignment of rows on one side of the tape can be opposite to the alignment of rows on the other side of the tape.

FIG. 3 illustrates variation in arrangements of protuberances 1 in overlaping patterns. The protuberances can form a zig-zag pattern on the tape.

In FIG. 4 the protuberances 1 are arranged in a curved patter.

DETAILED DESCRIPTION OF THE PREFERRED EMBODIMENT

Figure 1:
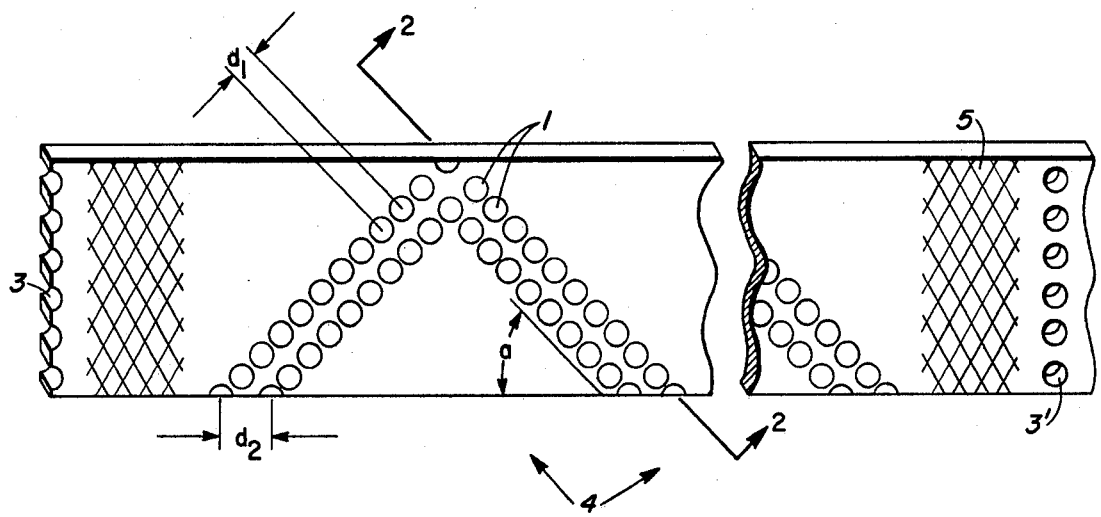
Figure 2:
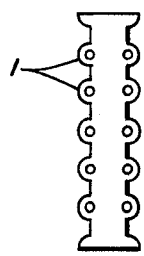
Figure 3:
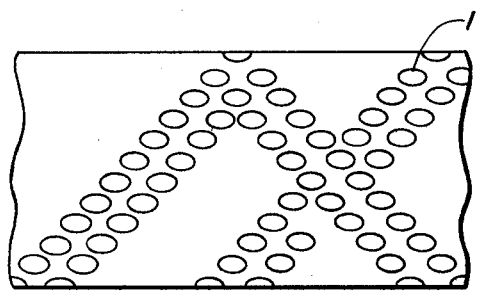
Figure 4:
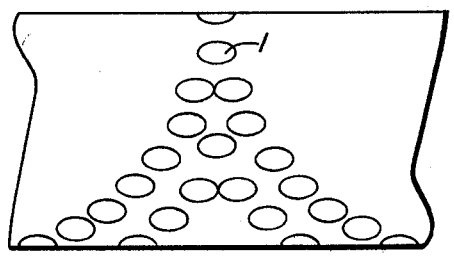

The tape width can vary from about 1 mm to about 10 mm, however, the preferred width is from about 2.5 to 7 mm. Tape width can be tailored to an individual's peridontal condition. The smallest width dimension provides optimum efficiency for individuals with periodontium within normal healthy limits. The wider variety of dental tape is best for individuals with more advanced stages of peridontitis. The more severe the peridontal disease existing, the wider the tape that may be prescribed by the dentist to effectively clean the exposed tooth and root surfaces.

A multitude of configurations of the plurality of protuberances are effective. They can be crosshatched, oblique from 10 to 80 degrees to the length of the tape, matrix, or film, with periodically reversed obliquity of the rows so that when the tape is moved in a sawing fasion, lift of the debris, i.e., debris is caught by the protuberances and travels along the oblique row of them down from the upper teeth and up from the lower teeth; or in other words, in a direction away from the gum, gingival, or base of the teeth towards the ends of the teeth, the lift is provided for in both the forward and the backward motion. However, protuberances arranged obliquely at about 45 degrees to the length of the tape have been found to be the most effective and is preferred.

The protuberances may be composed of a synthetic or natural fiber embedded within a synthetic or natural fiber, film, or matrix, or any combination thereof. Alternatively, the protuberances can be formed by means of heat and pressure upon the tape material by means known to the polymer art, whereby both the tape and protuberances are of the same material. The protuberances can be woven into said tape, matrix, film, or fiber, and may be synthetic or natural materials, and may be solid or hollow and any combination thereof.

Woven tape having woven protuberances have a combination of desirable characteristics, for example, strength, flex, give, grip, and good wear. It is preferred. However, from the economic point of view, polymeric film which is shaped and provided with protuberances by high speed pressing machinery known to the art is preferred. Dispensed from a roll, a proper length of tape for cleaning can be provided with ease of tearing by means of rows of perforations for removal from a roll and by other means known to the art. Moreover, the pressing machine can provide tape having a periodic knurling or other feature known to the art for gripping or preventing slippage between the fingers. In either case, protuberances can alternatively be provided by imbedded or sewn thread.

The tape and protuberances should not be so hard as to damage the user. A hardness of from about 0.3 Mohs to about 1.4 Mohs is workable, however, the preferred range of hardness is from about 0.5 to about 1.2 Mohs.

The thickness of the tape has been found to be important for it must allow adequate placement between tooth contacts and still be strong. On the average, the space between teeth ranges from about 1 mil to about 5 mils, however, a thickness of tape from about 1.5 mils to about 3 mils has been found to work best and have great utility. A tape thickness of from about 1.5 mils to about 3 mils is preferred.

The distance between the protuberances in a row can range from about 0.001 mm to about 3.0 mm, however, the preferred distance is from about 0.01 mm to about 3 mm.

The distance between rows can be as great as one to two inches or as little as 0.01 to 0.1 inch, however, the preferred distance between rows is from about ¼ to about ¾ of an inch. The smaller the distance the greater the chance of debris getting caught between rows. The larger the distance the greater the chance of debris falling through rather than being carried. The optimum lies inbetween and varies with user's speed of the tape motion.

The protuberances should preferably be arranged on both sides of the tape and at about the same angle off of the length of the tape. However, the protuberances can be different on either side of the tape although it is preferrable that they be the same to allow utilization of the tape effectively in any region of the mouth without changing sides of the tape for a given tooth surface.

The tape can have antiseptic and antibiotic properties by incorporating within the tape by means known to the polymer art, for instance, solution or plasticization, additives known to the art for delivering such properties although such properties are not necessary for cleaning. It is preferred that a pleasantly flavored antiseptic be incorporated within the tape to prevent reinoculation of Strep mutans and other pathogenic bacteria throughout the mouth. This further provides, at the very least, a bacteriostasis where placed interproximally. The flavoring will provide a pleasant flavor and odor after use.

The following examples are illustrative of the present invention but are not to be construed as limiting the invention thereto.

EXAMPLE 1

Knots of thread were sewn into a polyethyleneterephthalate tape to form approximately parallel rows of knots aligned approximately 45 degrees to the length of the tape, the knots of each row being about 0.01 mm apart and the rows being from about 1 mm apart to about 5 mm apart. This tape, having knotted thread protuberances, was placed between one of the inventor's two front teeth and drawn back and forth in a sawing fashion. Foreign matter between the teeth was caught by the knots and carried up the oblique row of them in a preferred direction away from the gums, gingival, or base of the teeth towards the ends of the teeth and away from the teeth. Subsequent tests showed that the treated tooth surfaces were free of plaque.

EXAMPLE 2

Knots of thread were sewn into a half inch wide cotton bandage tape, forming approximately parallel rows of knots aligned at about 30 degrees to the length of the tape. The distance between the knots in each row varied from about 0.2 mm to about 2 mm. Teeth were efficiently cleaned where the knots had rubbed against them.

EXAMPLE 3

By pressing the rounded tip of a small soldering iron against a quarter inch wide strip of nylon film rows of indentations being concave on the side where the iron pressed and protruding on the other side were made. The rows went up the width of the tape at about 45 degrees, reached the upper edge and then went down, forming a zig-zag pattern or a row of equilateral triangles. When the tape was pulled forward and backward between teeth, the zig-zag triangular pattern of fixed in place protuberances provided lift for some debris while other debris was deposited in the indentations of the film, that is, the debris was caught and held by the indentations.

It is obvious to those skilled in the art that modifications to our invention can be made without changing the scope or spirit thereof.

We claim:

1. A dental tape having length, width, edges and two sides for removing plaque from the teeth comprising a strong, flexible, tear-resistant tape having a multitude of rows of protuberances fixed in place which are aligned obliquely to the length of the tape, having preselected spacing between said rows and between said protuberances, and which lift debris in a preferred direction away from the base of the teeth towards the ends of the teeth, the debris riding along the rows aligned obliquely.

2. A dental tape according to claim 1 wherein each row of protuberances begins at one edge of said tape and ends at the other edge of said tape.

3. A dental tape according to claim 2 whrein said dental tape is non-tacky.

4. A dental tape according to claim 2 wherein said tape and said protuberances comprise substantially polymeric material.

5. A dental tape according to claim 4 wherein said protuberances are solid on both sides of said tape.

6. A dental tape according to claim 4 wherein said two sides have solid protuberances and indentations, said indentations capable of catching and holding debris.

7. A dental tape according to claim 4 wherein one side of said two sides has protuberances while the other side has indentations which are capable of catching and holding debris.

8. A dental tape according to claim 4 wherein said tape is periodically knurled for gripping and periodically perforated and dispensed from a roll.

9. A dental according to claim 4 wherein said rows are parallel to each other.

10. A dental tape according to claim 4 wherein the hardness of the protuberances is within the range of the hardness of plastics.

11. A dental tape according to claim 8 wherein said protuberances are solid on both sides of said tape.

12. A dental tape according to claim 8 wherein said two sides have solid protuberances and indentations which act as depositories for debris.

13. A dental tape according to claim 8 wherein said tape contains reinforcement, flavoring, and an antiseptic agent.

14. A dental tape according to claim 12 wherein said rows are arranged in a periodic zig-zag pattern.

15. A dental tape according to claim 4 wherein said protuberances are hollow and have give.

16. A dental tape according to claim 5 wherein said rows have periodically reversed obliquity.

17. A dental tape according to claim 5 wherein said rows have a variety of obliquities.

18. A dental tape having length, preselected width, edges and two sides for removing plaque from the teeth comprising a strong, flexible, non-tacky in storage and in use, tear-resistant tape having a multitude of rows of protuberances fixed in place which are aligned obliquely to the length of the tape at preselected angles, and have preselected spacing, and wherein each row of protuberances begins at one edge of said tape and proceeds along an angular line across the width of said tape.

19. A dental tape having length, preselected width, edges and two sides for removing plaque from the teeth comprising a strong, flexible, non-tacky, tear-resistant tape having a multitude of rows of protuberances which are fixed in place and aligned obliquely at preselected angle to the length of the tape and have preselected spacing between rows and protuberances, the oblique alignment of protuberances lift debris in a direction away from the gum, the rows of protuberances beginning at one edge of said tape and ending at the other edge of said tape, a preselected number of protuberances being hollow and having give, a preselected number of protuberances protruding on one side of the tape and indented on the other, the tape and protuberances being within the range of plastic hardness, the tape being periodically knurled for gripping, periodically perforated for ease of separation, and dispensed from a roll, the tape, perforations, knurled gripping, periodic indentations being of the same material, said indentations acting as depositories for debris.

* * * * *